(12) United States Patent  
Doubler et al.

(10) Patent No.: US 7,942,911 B2
(45) Date of Patent: May 17, 2011

(54) POLYAXIAL BONE SCREW

(75) Inventors: Robert L. Doubler, Monroe, MI (US);
John E. Hammill, Rossford, OH (US)

(73) Assignee: Ortho Innovations, LLC, Palm Beach Gardens, FL (US)

( * ) Notice: Subject to any disclaimer, the term of this patent is extended or adjusted under 35 U.S.C. 154(b) by 116 days.

(21) Appl. No.: 12/484,054

(22) Filed: Jun. 12, 2009

(65) Prior Publication Data
US 2009/0306720 A1 Dec. 10, 2009

Related U.S. Application Data

(63) Continuation-in-part of application No. 11/749,615, filed on May 16, 2007.

(51) Int. Cl.
*A61B 17/70* (2006.01)

(52) U.S. Cl. ........ 606/269; 606/265; 606/267; 606/270; 606/306

(58) Field of Classification Search .......... 606/264–275, 606/300, 301, 305–308
See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,419,026 A | 12/1983 | Leto |
| 4,483,334 A | 11/1984 | Murray |
| 4,570,982 A | 2/1986 | Blose et al. |
| 4,693,240 A | 9/1987 | Evans |
| 4,708,510 A | 11/1987 | McConnell et al. |
| 4,763,644 A | 8/1988 | Webb |
| 4,805,602 A | 2/1989 | Puno et al. |
| 4,836,196 A | 6/1989 | Park et al. |
| 4,841,959 A | 6/1989 | Ransford |
| 4,854,304 A | 8/1989 | Zielke |
| 4,867,144 A | 9/1989 | Karas et al. |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,005,562 A | 4/1991 | Cotrel |
| 5,084,049 A | 1/1992 | Asher et al. |
| 5,085,660 A | 2/1992 | Lin |
| 5,092,893 A | 3/1992 | Smith |
| 5,129,388 A | 7/1992 | Vignaud et al. |
| 5,129,900 A | 7/1992 | Asher et al. |
| 5,133,716 A | 7/1992 | Plaza |

(Continued)

FOREIGN PATENT DOCUMENTS

DE G9202745.8 4/1992

(Continued)

*Primary Examiner* — Eduardo C Robert
*Assistant Examiner* — Ellen C Hammond
(74) *Attorney, Agent, or Firm* — McHale & Slavin, P.A.

(57) ABSTRACT

A fastening system for bone screws used in spinal fixation systems for reshaping the spine of a patient. The bone screw has threads on one end for anchoring in the spine. The other end has a spherical head with a multi sided recess formed therein for engagement with an appropriate driving tool. The system includes a stabilizing rod, a saddle member, a cap member and a set screw with at least one bone screw having a outer diameter that exceeds the diameter of a cavity formed in the saddle, wherein placement of the bone screw is made possible by matching the threads of the set screw to the threads of the bone screw. The head of the bone screw providing proper positioning of the stabilization rod within the patient.

24 Claims, 9 Drawing Sheets

U.S. PATENT DOCUMENTS

| | | | |
|---|---|---|---|
| 5,133,717 A | 7/1992 | Chopin | |
| 5,176,678 A | 1/1993 | Tsou | |
| 5,207,678 A | 5/1993 | Harms et al. | |
| 5,217,497 A | 6/1993 | Mehdian | |
| 5,257,993 A | 11/1993 | Asher et al. | |
| 5,261,909 A | 11/1993 | Sutterlin et al. | |
| 5,261,912 A | 11/1993 | Frigg | |
| 5,312,404 A | 5/1994 | Asher et al. | |
| 5,312,405 A | 5/1994 | Korotko et al. | |
| 5,330,477 A | 7/1994 | Crook | |
| 5,360,431 A | 11/1994 | Puno et al. | |
| 5,364,399 A | 11/1994 | Lowery et al. | |
| 5,395,371 A | 3/1995 | Miller et al. | |
| 5,429,639 A | 7/1995 | Judet | |
| 5,437,671 A | 8/1995 | Lozier et al. | |
| 5,443,467 A * | 8/1995 | Biedermann et al. | 606/65 |
| 5,466,237 A | 11/1995 | Byrd, III et al. | |
| 5,470,333 A | 11/1995 | Ray | |
| 5,474,555 A | 12/1995 | Puno et al. | |
| 5,476,462 A | 12/1995 | Allard et al. | |
| 5,476,464 A | 12/1995 | Metz-Stavenhagen et al. | |
| 5,480,401 A | 1/1996 | Navas | |
| 5,496,321 A | 3/1996 | Puno et al. | |
| 5,498,262 A | 3/1996 | Bryan | |
| 5,498,263 A | 3/1996 | DiNello et al. | |
| 5,501,684 A | 3/1996 | Schlapfer et al. | |
| 5,520,690 A | 5/1996 | Errico et al. | |
| 5,527,314 A | 6/1996 | Brumfield et al. | |
| 5,531,746 A | 7/1996 | Errico et al. | |
| 5,545,164 A | 8/1996 | Howland | |
| 5,549,608 A | 8/1996 | Errico et al. | |
| 5,554,157 A | 9/1996 | Errico et al. | |
| 5,562,661 A | 10/1996 | Yoshimi et al. | |
| 5,569,247 A | 10/1996 | Morrison | |
| 5,575,792 A | 11/1996 | Errico et al. | |
| 5,578,033 A | 11/1996 | Errico et al. | |
| 5,584,834 A | 12/1996 | Errico et al. | |
| 5,586,984 A | 12/1996 | Errico et al. | |
| 5,591,165 A | 1/1997 | Jackson | |
| 5,591,166 A | 1/1997 | Bernhardt et al. | |
| 5,601,552 A | 2/1997 | Cotrel | |
| 5,601,553 A | 2/1997 | Trebing et al. | |
| 5,607,426 A | 3/1997 | Ralph et al. | |
| 5,609,593 A | 3/1997 | Errico et al. | |
| 5,609,594 A | 3/1997 | Errico et al. | |
| 5,628,740 A | 5/1997 | Mullane | |
| 5,643,261 A | 7/1997 | Schafer et al. | |
| 5,643,265 A | 7/1997 | Errico et al. | |
| 5,647,873 A | 7/1997 | Errico et al. | |
| 5,669,910 A | 9/1997 | Korhonen et al. | |
| 5,669,911 A | 9/1997 | Errico et al. | |
| 5,672,176 A | 9/1997 | Biedermann et al. | |
| 5,681,319 A | 10/1997 | Biedermann et al. | |
| 5,688,272 A | 11/1997 | Montagne et al. | |
| 5,688,273 A | 11/1997 | Errico et al. | |
| 5,690,630 A | 11/1997 | Errico et al. | |
| 5,716,355 A | 2/1998 | Jackson et al. | |
| 5,716,356 A | 2/1998 | Biedermann et al. | |
| 5,716,357 A | 2/1998 | Rogozinski | |
| 5,725,528 A | 3/1998 | Errico et al. | |
| 5,725,588 A | 3/1998 | Errico et al. | |
| 5,728,098 A | 3/1998 | Sherman et al. | |
| 5,733,286 A | 3/1998 | Errico et al. | |
| 5,738,685 A | 4/1998 | Halm et al. | |
| 5,782,833 A | 7/1998 | Haider | |
| 5,797,911 A | 8/1998 | Sherman et al. | |
| 5,800,435 A | 9/1998 | Errico et al. | |
| 5,810,818 A | 9/1998 | Errico et al. | |
| 5,817,094 A | 10/1998 | Errico et al. | |
| 5,863,293 A | 1/1999 | Richelsoph | |
| 5,873,878 A | 2/1999 | Harms et al. | |
| 5,876,402 A | 3/1999 | Errico et al. | |
| 5,879,350 A | 3/1999 | Sherman et al. | |
| 5,879,351 A | 3/1999 | Viart | |
| 5,882,350 A | 3/1999 | Ralph et al. | |
| 5,885,286 A | 3/1999 | Sherman et al. | |
| 5,891,145 A | 4/1999 | Morrison et al. | |
| 5,902,303 A | 5/1999 | Eckhof et al. | |
| 5,947,966 A | 9/1999 | Drewry et al. | |
| 5,954,725 A | 9/1999 | Sherman et al. | |
| 5,961,517 A | 10/1999 | Biedermann et al. | |
| 5,964,760 A | 10/1999 | Richelsoph | |
| 5,980,523 A | 11/1999 | Jackson | |
| 6,010,503 A | 1/2000 | Richelsoph et al. | |
| 6,015,409 A | 1/2000 | Jackson | |
| 6,019,759 A | 2/2000 | Rogozinski | |
| 6,022,350 A | 2/2000 | Ganem | |
| 6,050,997 A | 4/2000 | Mullane | |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,080,156 A | 6/2000 | Asher et al. | |
| 6,086,588 A | 7/2000 | Ameil et al. | |
| 6,090,110 A | 7/2000 | Metz-Stavenhagen | |
| 6,090,111 A | 7/2000 | Nichols | |
| 6,099,528 A | 8/2000 | Saurat | |
| 6,110,172 A | 8/2000 | Jackson | |
| 6,113,600 A | 9/2000 | Drummond et al. | |
| 6,113,601 A | 9/2000 | Tatar | |
| 6,132,431 A | 10/2000 | Nilsson et al. | |
| 6,132,432 A | 10/2000 | Richelsoph | |
| 6,132,434 A | 10/2000 | Sherman et al. | |
| 6,146,383 A | 11/2000 | Studer et al. | |
| 6,183,472 B1 | 2/2001 | Lutz | |
| 6,187,005 B1 | 2/2001 | Brace et al. | |
| RE37,161 E | 5/2001 | Michelson et al. | |
| 6,224,596 B1 | 5/2001 | Jackson | |
| 6,248,105 B1 | 6/2001 | Schlapfer et al. | |
| 6,254,602 B1 | 7/2001 | Justis | |
| 6,261,287 B1 | 7/2001 | Metz-Stavenhagen | |
| 6,273,888 B1 | 8/2001 | Justis | |
| 6,280,442 B1 | 8/2001 | Barker et al. | |
| 6,280,445 B1 | 8/2001 | Morrison et al. | |
| 6,287,308 B1 | 9/2001 | Betz et al. | |
| 6,287,311 B1 | 9/2001 | Sherman et al. | |
| 6,296,642 B1 | 10/2001 | Morrison et al. | |
| 6,302,888 B1 | 10/2001 | Mellinger et al. | |
| 6,309,391 B1 | 10/2001 | Crandall et al. | |
| 6,331,179 B1 | 12/2001 | Freid et al. | |
| 6,355,040 B1 | 3/2002 | Richelsoph et al. | |
| RE37,665 E | 4/2002 | Ralph et al. | |
| 6,368,321 B1 * | 4/2002 | Jackson | 606/270 |
| 6,383,190 B1 | 5/2002 | Preissman | |
| 6,402,752 B2 | 6/2002 | Schaffler-Wachter et al. | |
| 6,436,100 B1 | 8/2002 | Berger | |
| 6,440,137 B1 | 8/2002 | Horvath et al. | |
| 6,451,021 B1 | 9/2002 | Ralph et al. | |
| 6,471,703 B1 | 10/2002 | Ashman | |
| 6,471,705 B1 | 10/2002 | Biedermann et al. | |
| 6,485,491 B1 | 11/2002 | Farris | |
| 6,485,494 B1 | 11/2002 | Haider | |
| 6,488,681 B2 | 12/2002 | Martin et al. | |
| 6,508,818 B2 | 1/2003 | Steiner et al. | |
| 6,520,962 B1 | 2/2003 | Taylor et al. | |
| 6,527,804 B1 | 3/2003 | Gauchet et al. | |
| 6,530,929 B1 | 3/2003 | Justis et al. | |
| 6,533,786 B1 | 3/2003 | Needham et al. | |
| 6,537,276 B2 | 3/2003 | Metz-Stavenhagen | |
| 6,547,789 B1 | 4/2003 | Ventre et al. | |
| 6,547,790 B2 | 4/2003 | Harkey, III et al. | |
| 6,551,320 B2 | 4/2003 | Liebermann | |
| 6,554,832 B2 | 4/2003 | Shluzas | |
| 6,554,834 B1 | 4/2003 | Crozet et al. | |
| 6,558,387 B2 | 5/2003 | Errico et al. | |
| 6,562,040 B1 | 5/2003 | Wagner | |
| 6,565,565 B1 | 5/2003 | Yuan et al. | |
| 6,565,567 B1 | 5/2003 | Haider | |
| 6,582,436 B2 | 6/2003 | Schlapfer et al. | |
| 6,582,466 B1 | 6/2003 | Gauchet | |
| 6,585,740 B2 | 7/2003 | Schlapfer et al. | |
| 6,595,992 B1 | 7/2003 | Wagner et al. | |
| 6,595,993 B2 | 7/2003 | Donno et al. | |
| 6,610,063 B2 | 8/2003 | Kumar et al. | |
| 6,613,050 B1 | 9/2003 | Wagner et al. | |
| 6,623,485 B2 | 9/2003 | Doubler et al. | |
| 6,626,907 B2 | 9/2003 | Campbell et al. | |

| | | | | | | |
|---|---|---|---|---|---|---|
| 6,626,908 B2 | 9/2003 | Cooper et al. | 7,445,627 B2 | 11/2008 | Hawkes et al. | |
| 6,635,059 B2 | 10/2003 | Randall et al. | 7,604,656 B2 | 10/2009 | Shluzas | |
| 6,641,586 B2 | 11/2003 | Varieur | 7,682,377 B2 | 3/2010 | Konieczynski | |
| 6,648,885 B1 | 11/2003 | Friesem | 2001/0001119 A1 | 5/2001 | Lombardo | |
| 6,648,887 B2 | 11/2003 | Ashman | 2002/0035366 A1 | 3/2002 | Walder et al. | |
| 6,656,179 B1 | 12/2003 | Schaefer et al. | 2002/0045898 A1 | 4/2002 | Freid et al. | |
| 6,656,181 B2 | 12/2003 | Dixon et al. | 2002/0082602 A1 | 6/2002 | Biedermann et al. | |
| 6,660,004 B2 | 12/2003 | Barker et al. | 2002/0103487 A1 | 8/2002 | Errico et al. | |
| 6,663,632 B1 | 12/2003 | Frigg | 2002/0111626 A1 | 8/2002 | Ralph et al. | |
| 6,663,635 B2 | 12/2003 | Frigg et al. | 2002/0143341 A1 | 10/2002 | Biedermann et al. | |
| 6,672,788 B2 | 1/2004 | Hathaway | 2002/0173789 A1 | 11/2002 | Howland | |
| 6,673,073 B1 | 1/2004 | Schafer | 2002/0193795 A1 | 12/2002 | Gertzbein et al. | |
| 6,676,661 B1 | 1/2004 | Martin Benlloch et al. | 2003/0004512 A1 | 1/2003 | Farris et al. | |
| 6,679,833 B2 | 1/2004 | Smith et al. | 2003/0023243 A1 | 1/2003 | Biedermann et al. | |
| 6,682,529 B2 | 1/2004 | Stahurski | 2003/0045879 A1 | 3/2003 | Minfelde et al. | |
| 6,689,133 B2 | 2/2004 | Morrison et al. | 2003/0073996 A1 | 4/2003 | Doubler et al. | |
| 6,689,134 B2 | 2/2004 | Ralph et al. | 2003/0093078 A1 | 5/2003 | Ritland | |
| 6,695,843 B2 | 2/2004 | Biedermann et al. | 2003/0100896 A1 | 5/2003 | Biedermann et al. | |
| 6,695,851 B2 | 2/2004 | Zdeblick et al. | 2003/0105460 A1 | 6/2003 | Crandall et al. | |
| 6,699,249 B2 | 3/2004 | Schlapfer et al. | 2003/0118395 A1 | 6/2003 | Abels et al. | |
| 6,706,045 B2 | 3/2004 | Lin et al. | 2003/0125741 A1 | 7/2003 | Biedermann et al. | |
| 6,712,818 B1 | 3/2004 | Michelson | 2003/0149432 A1 | 8/2003 | Frigg et al. | |
| 6,716,213 B2 | 4/2004 | Shitoto | 2003/0163133 A1 | 8/2003 | Altarac et al. | |
| 6,716,214 B1 | 4/2004 | Jackson | 2003/0176862 A1 | 9/2003 | Taylor et al. | |
| 6,716,247 B2 | 4/2004 | Michelson | 2003/0199873 A1 | 10/2003 | Richelsoph | |
| 6,723,100 B2 | 4/2004 | Biedermann et al. | 2003/0208204 A1 | 11/2003 | Bailey et al. | |
| 6,726,689 B2 | 4/2004 | Jackson | 2003/0216735 A1 | 11/2003 | Altarac et al. | |
| 6,730,093 B2 | 5/2004 | St. Martin | 2004/0006342 A1 | 1/2004 | Altarac et al. | |
| 6,730,127 B2 | 5/2004 | Michelson | 2004/0024464 A1 | 2/2004 | Errico et al. | |
| 6,733,502 B2 | 5/2004 | Altarac et al. | 2004/0092934 A1 | 5/2004 | Howland | |
| 6,736,816 B2 | 5/2004 | Ritland | 2004/0097933 A1 | 5/2004 | Lourdel et al. | |
| 6,736,820 B2 | 5/2004 | Biedermann et al. | 2004/0102781 A1 | 5/2004 | Jeon | |
| 6,740,086 B2 | 5/2004 | Richelsoph | 2004/0116929 A1 | 6/2004 | Barker et al. | |
| 6,746,449 B2 | 6/2004 | Jones et al. | 2004/0127906 A1 | 7/2004 | Culbert et al. | |
| 6,755,829 B1 | 6/2004 | Bono et al. | 2004/0138662 A1 | 7/2004 | Landry et al. | |
| 6,755,830 B2 | 6/2004 | Minfelde et al. | 2004/0143265 A1 | 7/2004 | Landry et al. | |
| 6,755,835 B2 | 6/2004 | Schultheiss et al. | 2004/0147929 A1 | 7/2004 | Biedermann et al. | |
| 6,755,836 B1 | 6/2004 | Lewis | 2004/0158247 A1 | 8/2004 | Sitiso et al. | |
| 6,761,723 B2 | 7/2004 | Butterman et al. | 2004/0172022 A1 | 9/2004 | Landry et al. | |
| 6,767,351 B2 | 7/2004 | Orbay et al. | 2004/0176766 A1 | 9/2004 | Shluzas | |
| 6,770,075 B2 | 8/2004 | Howland | 2004/0186473 A1 | 9/2004 | Cournoyer et al. | |
| 6,780,186 B2 | 8/2004 | Errico et al. | 2004/0193160 A1 | 9/2004 | Richelsoph | |
| 6,790,209 B2 | 9/2004 | Beale et al. | 2004/0210216 A1 | 10/2004 | Farris et al. | |
| 6,827,719 B2 | 12/2004 | Ralph et al. | 2004/0225289 A1 | 11/2004 | Biedermann et al. | |
| 6,830,571 B2 | 12/2004 | Lenke et al. | 2004/0236330 A1 | 11/2004 | Purcell et al. | |
| 6,835,196 B2 | 12/2004 | Biedermann et al. | 2004/0249380 A1 | 12/2004 | Glascott | |
| 6,837,889 B2 | 1/2005 | Shluzas | 2004/0267264 A1* | 12/2004 | Konieczynski et al. | 606/73 |
| 6,840,940 B2 | 1/2005 | Ralph et al. | 2005/0027296 A1 | 2/2005 | Thramann et al. | |
| 6,843,791 B2 | 1/2005 | Serhan | 2005/0033289 A1 | 2/2005 | Warren et al. | |
| 6,858,031 B2 | 2/2005 | Morrison et al. | 2005/0055026 A1 | 3/2005 | Biedermann et al. | |
| 6,869,432 B2 | 3/2005 | Schlapfer et al. | 2005/0070899 A1 | 3/2005 | Doubler et al. | |
| 6,869,433 B2 | 3/2005 | Glascott | 2005/0080415 A1 | 4/2005 | Keyer et al. | |
| 6,872,208 B1 | 3/2005 | McBride et al. | 2005/0107788 A1 | 5/2005 | Beaurain et al. | |
| 6,905,500 B2 | 6/2005 | Jeon et al. | 2005/0113927 A1 | 5/2005 | Malek | |
| 6,932,817 B2 | 8/2005 | Baynham et al. | 2005/0131404 A1 | 6/2005 | Mazda et al. | |
| 6,945,972 B2 | 9/2005 | Frigg et al. | 2005/0131409 A1 | 6/2005 | Chervitz et al. | |
| 6,950,997 B2 | 9/2005 | Dickey | 2005/0131413 A1 | 6/2005 | O'Driscoll et al. | |
| 6,951,561 B2 | 10/2005 | Warren et al. | 2005/0131537 A1 | 6/2005 | Hoy et al. | |
| 6,953,462 B2 | 10/2005 | Lieberman | 2005/0131538 A1 | 6/2005 | Chervitz et al. | |
| 6,955,677 B2 | 10/2005 | Dahners | 2005/0131545 A1 | 6/2005 | Chervitz et al. | |
| 6,958,065 B2 | 10/2005 | Ueyama et al. | 2005/0149023 A1 | 7/2005 | Ritland | |
| 6,964,664 B2 | 11/2005 | Freid et al. | 2005/0154389 A1 | 7/2005 | Selover et al. | |
| 6,964,665 B2 | 11/2005 | Thomas et al. | 2005/0154391 A1 | 7/2005 | Doherty et al. | |
| 6,974,460 B2 | 12/2005 | Carbone et al. | 2005/0159750 A1 | 7/2005 | Doherty | |
| 6,979,334 B2 | 12/2005 | Dalton | 2005/0165400 A1 | 7/2005 | Fernandez | |
| 6,981,973 B2 | 1/2006 | McKinley | 2005/0171540 A1 | 8/2005 | Lim et al. | |
| RE39,035 E | 3/2006 | Finn et al. | 2005/0187548 A1 | 8/2005 | Butler et al. | |
| 7,018,378 B2 | 3/2006 | Biedermann et al. | 2005/0187555 A1 | 8/2005 | Biedermann et al. | |
| 7,018,379 B2 | 3/2006 | Drewry et al. | 2005/0192571 A1 | 9/2005 | Abdelgany | |
| RE39,089 E | 5/2006 | Ralph et al. | 2005/0192580 A1 | 9/2005 | Dalton | |
| 7,066,937 B2 | 6/2006 | Shluzas | 2005/0203515 A1 | 9/2005 | Doherty et al. | |
| 7,087,057 B2 | 8/2006 | Konieczynski et al. | 2005/0203516 A1 | 9/2005 | Biedermann et al. | |
| 7,128,743 B2 | 10/2006 | Metz-Stavenhagen | 2005/0216003 A1 | 9/2005 | Biedermann et al. | |
| 7,144,396 B2 | 12/2006 | Shluzas | 2005/0228392 A1 | 10/2005 | Keyer et al. | |
| 7,163,538 B2 | 1/2007 | Altarac et al. | 2005/0228501 A1 | 10/2005 | Miller et al. | |
| 7,223,268 B2 | 5/2007 | Biedermann | 2005/0234450 A1 | 10/2005 | Barker | |
| 7,306,606 B2 | 12/2007 | Sasing | 2005/0234451 A1 | 10/2005 | Markworth | |
| 7,322,981 B2 | 1/2008 | Jackson | 2005/0234452 A1 | 10/2005 | Malandain | |
| 7,335,202 B2 | 2/2008 | Matthis et al. | 2005/0240181 A1 | 10/2005 | Boomer et al. | |

| | | |
|---|---|---|
| 2005/0240183 A1 | 10/2005 | Vaughan |
| 2005/0251137 A1 | 11/2005 | Ball |
| 2005/0251141 A1 | 11/2005 | Frigg et al. |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0015105 A1 | 1/2006 | Warren et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0084979 A1* | 4/2006 | Jackson .................. 606/61 |
| 2006/0149240 A1 | 7/2006 | Jackson |
| 2006/0149241 A1 | 7/2006 | Richelsoph |
| 2006/0155277 A1 | 7/2006 | Metz-Stavenhagen |
| 2006/0235392 A1 | 10/2006 | Hammer et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0276791 A1 | 12/2006 | Shluzas |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi et al. |
| 2008/0009862 A1 | 1/2008 | Hoffman |
| 2008/0015576 A1 | 1/2008 | Whipple |
| 2008/0015579 A1 | 1/2008 | Whipple |
| 2008/0015580 A1 | 1/2008 | Chao |
| 2008/0015597 A1 | 1/2008 | Whipple |
| 2008/0045953 A1 | 2/2008 | Garamszegi |
| 2008/0086132 A1* | 4/2008 | Biedermann et al. .......... 606/61 |
| 2008/0097436 A1 | 4/2008 | Culbert et al. |
| 2008/0177322 A1 | 7/2008 | Davis et al. |
| 2008/0269809 A1 | 10/2008 | Garamszegi |
| 2008/0287998 A1 | 11/2008 | Doubler et al. |
| 2009/0163956 A1 | 6/2009 | Biedermann et al. |

FOREIGN PATENT DOCUMENTS

| | | |
|---|---|---|
| DE | 19509332 | 8/1996 |
| DE | 19507141 | 9/1996 |
| DE | 19720782 | 12/2004 |
| EP | 1121902 | 8/2001 |
| EP | 1190678 | 3/2002 |
| EP | 1474050 | 11/2004 |
| EP | 1570795 | 9/2005 |
| EP | 1579816 | 9/2005 |
| EP | 1634537 | 3/2006 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 2173104 | 10/1986 |
| GB | 2365345 | 2/2002 |
| WO | WO01/49191 | 7/2001 |
| WO | WO02/054966 | 7/2002 |
| WO | WO03/068088 | 8/2003 |
| WO | WO03068083 | 8/2003 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/012088 | 2/2006 |
| WO | WO2006/017616 | 2/2006 |
| WO | WO2006/028537 | 3/2006 |

* cited by examiner

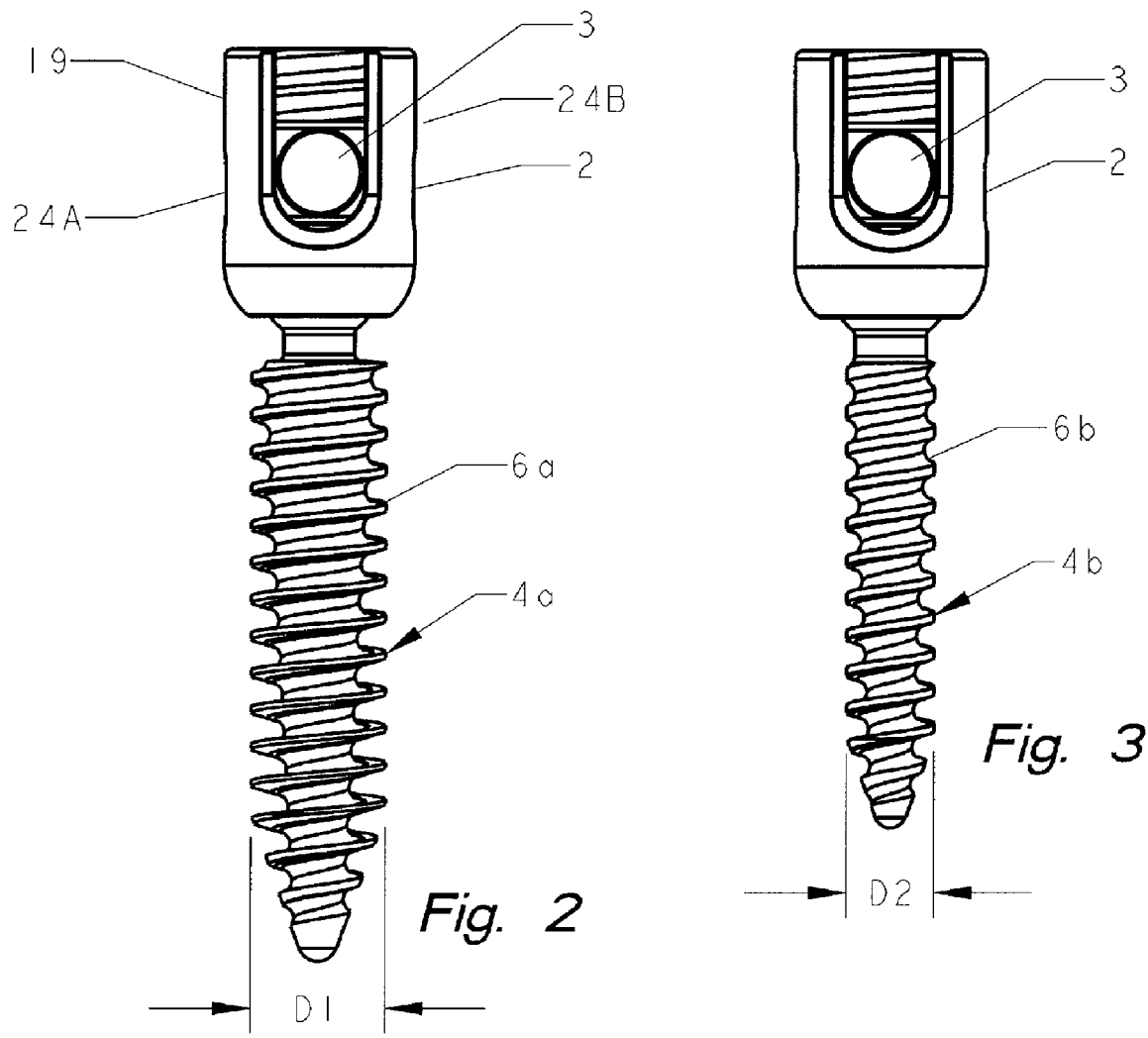
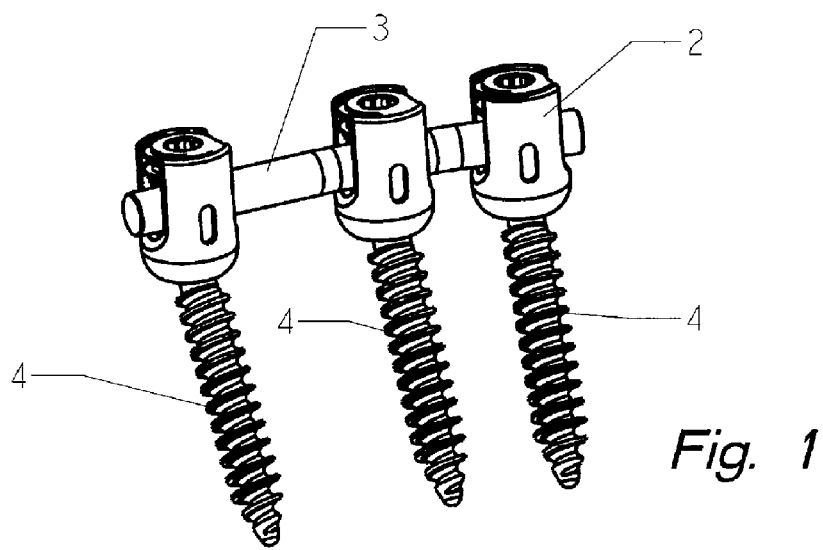

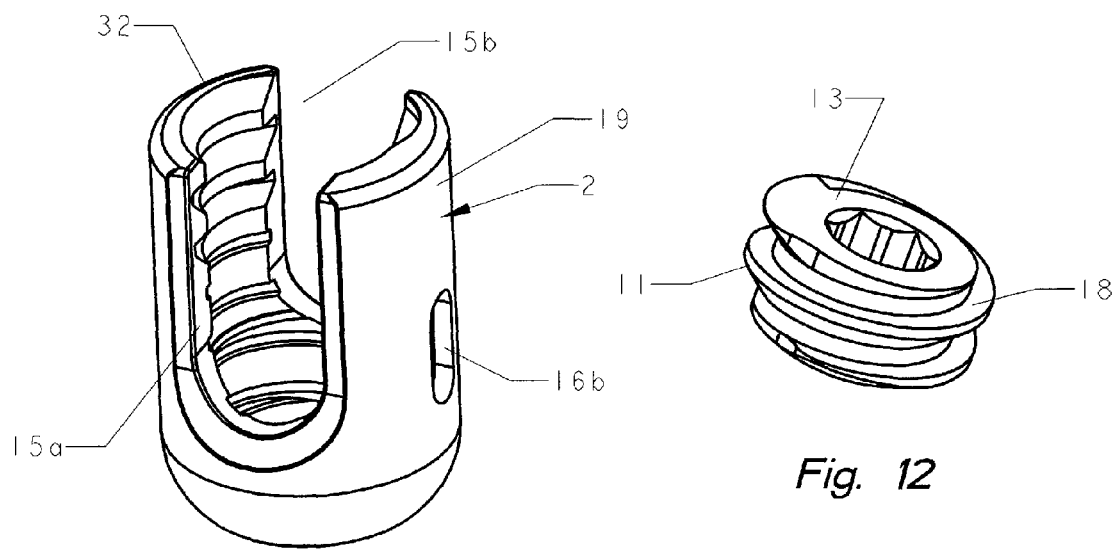
Fig. 10
Fig. 12
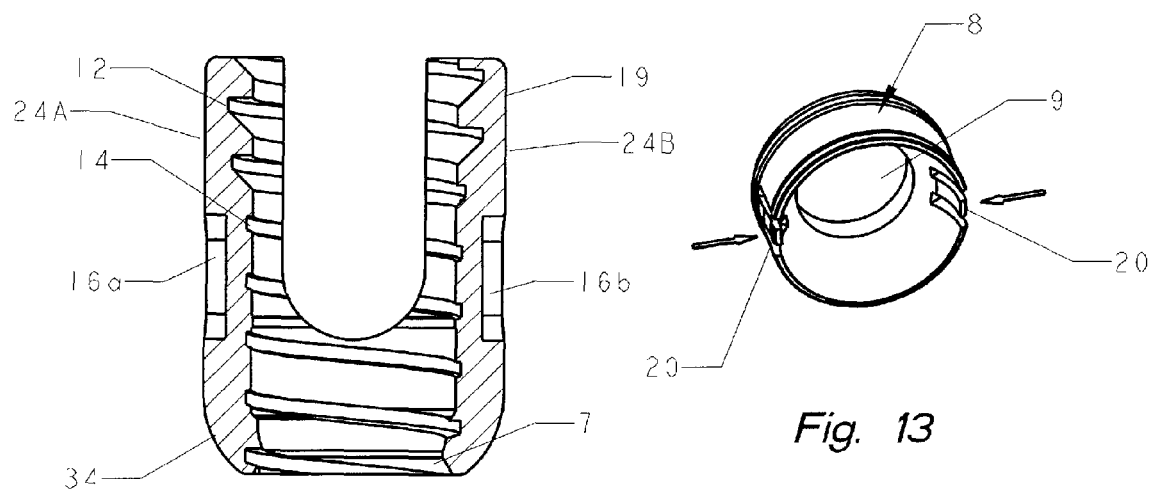
Fig. 11
Fig. 13

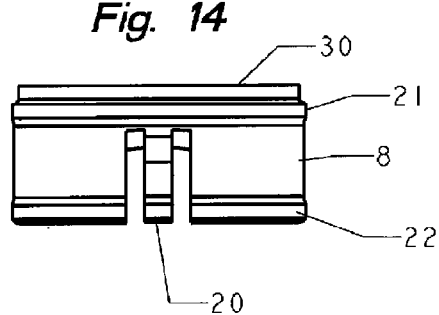
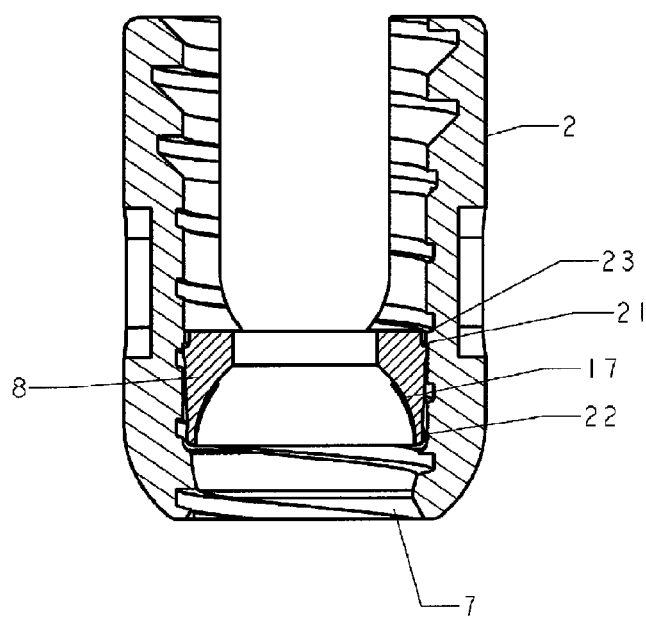
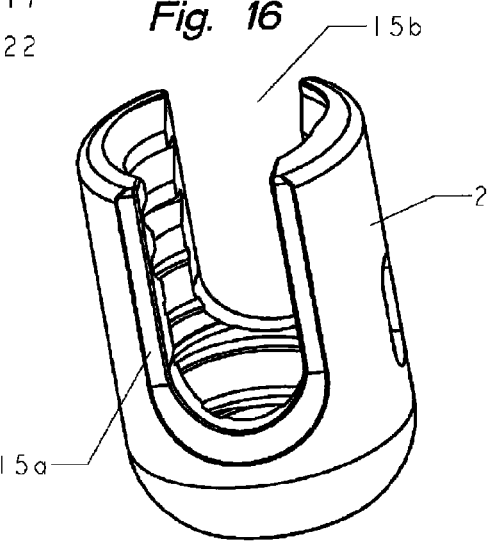
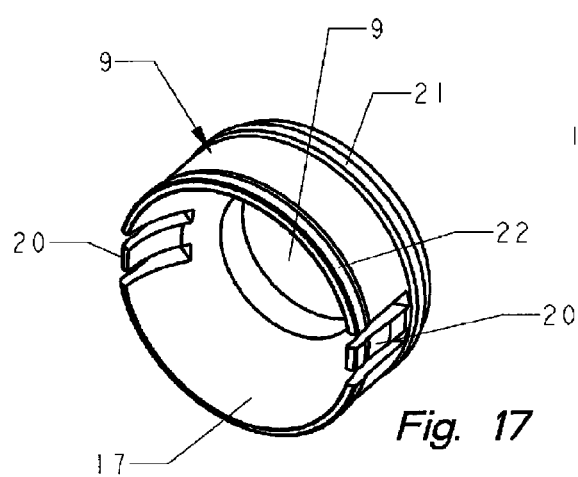

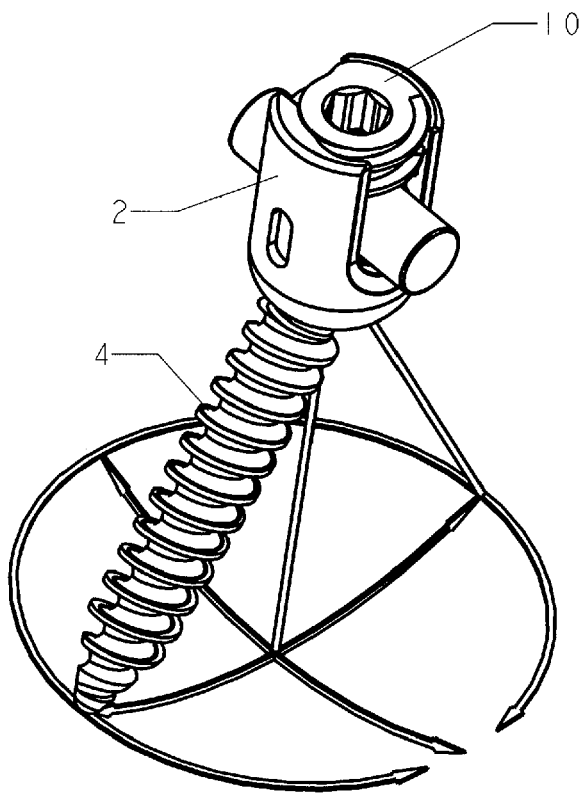
Fig. 18
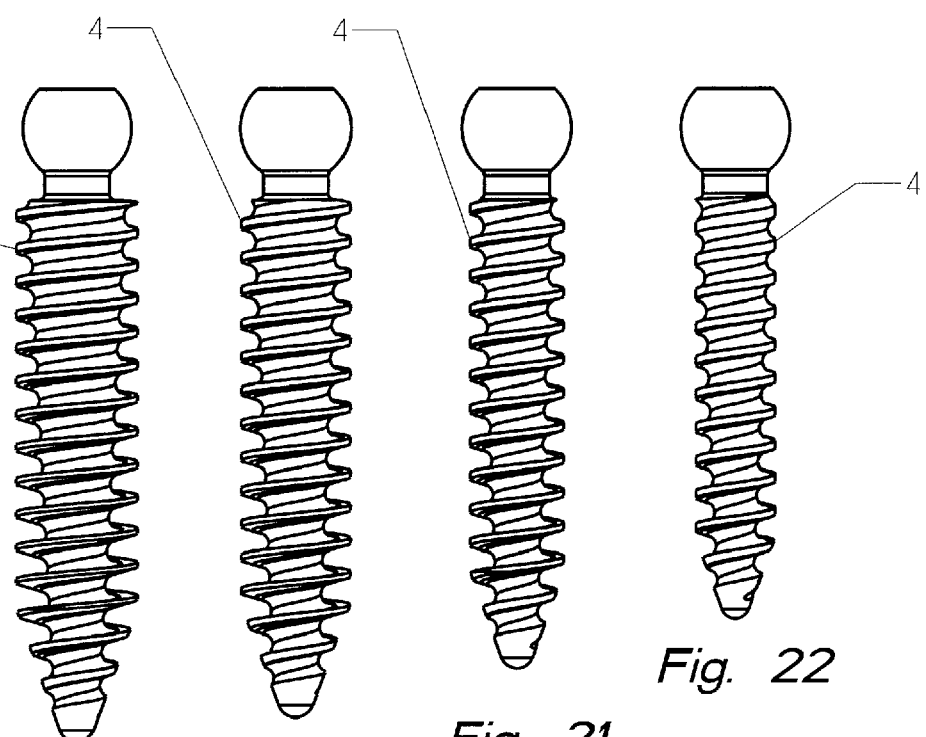
Fig. 19
Fig. 20
Fig. 21
Fig. 22

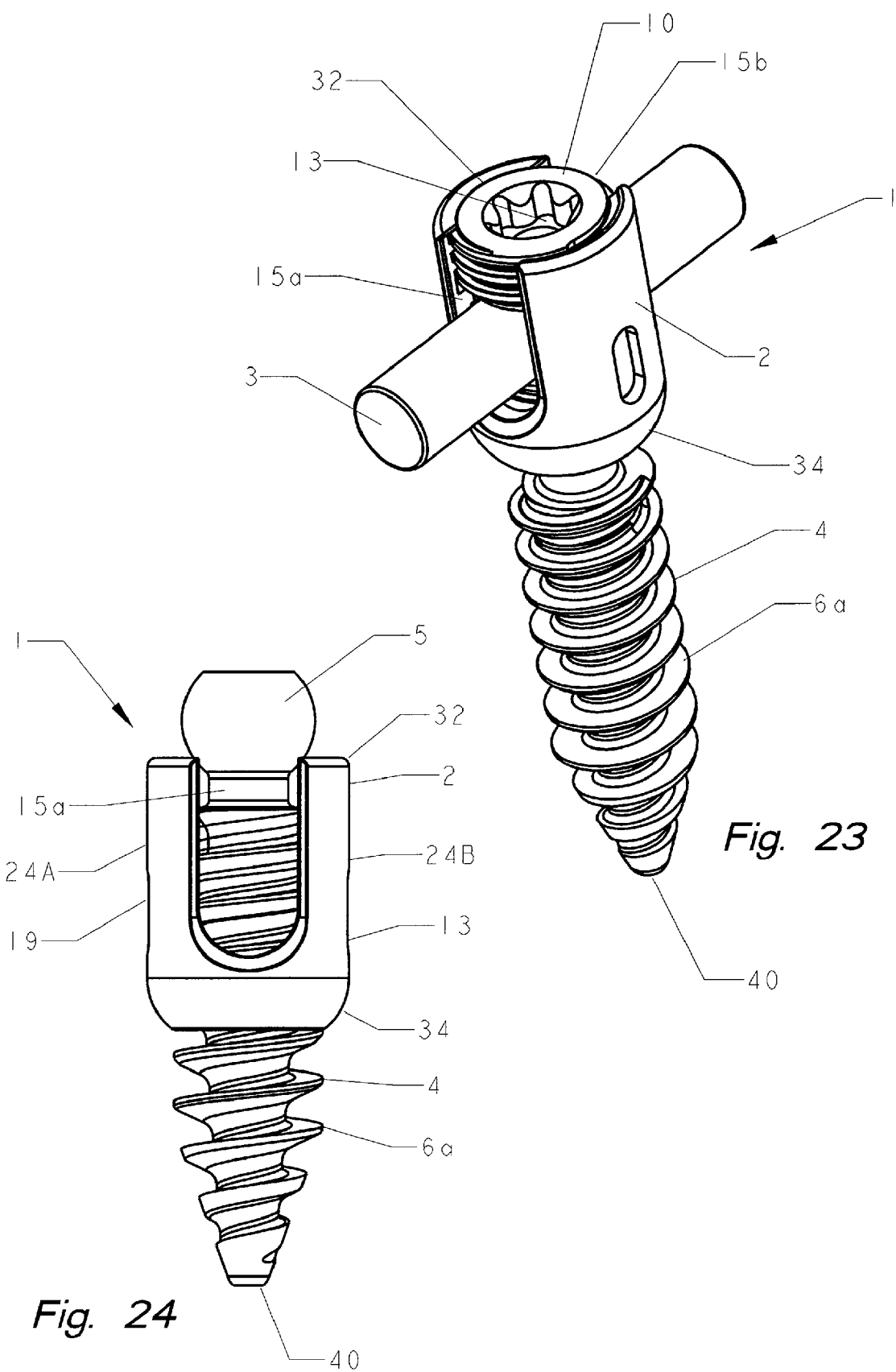

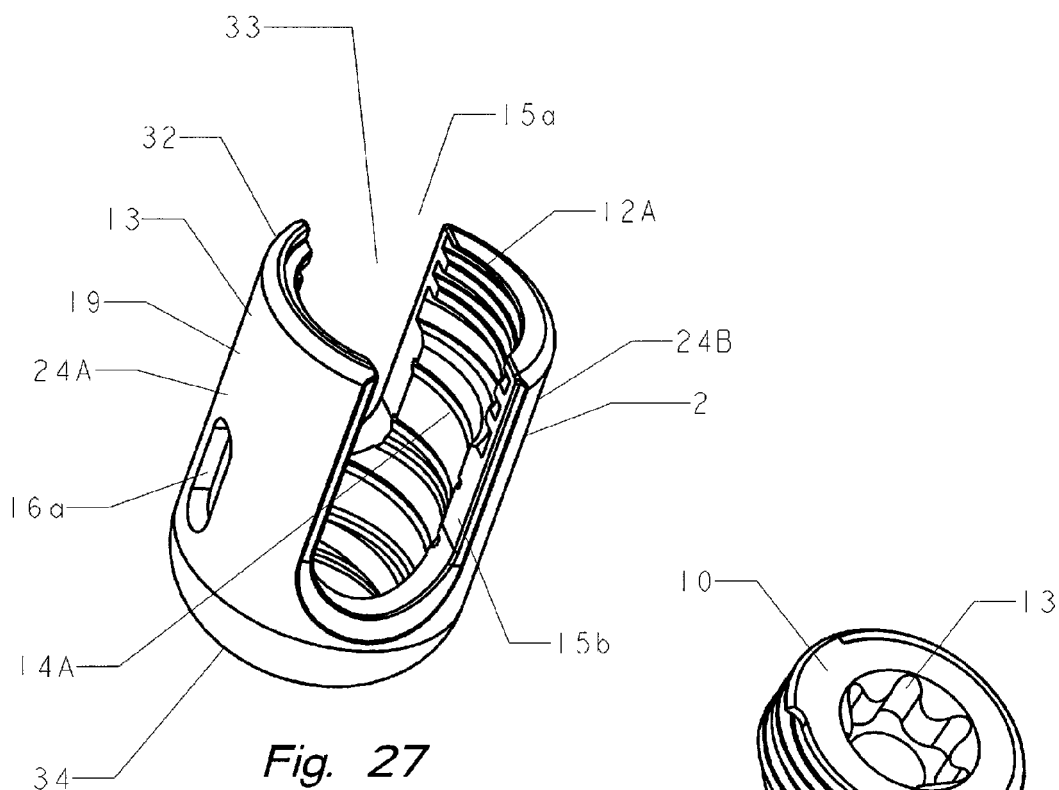
Fig. 27
Fig. 28
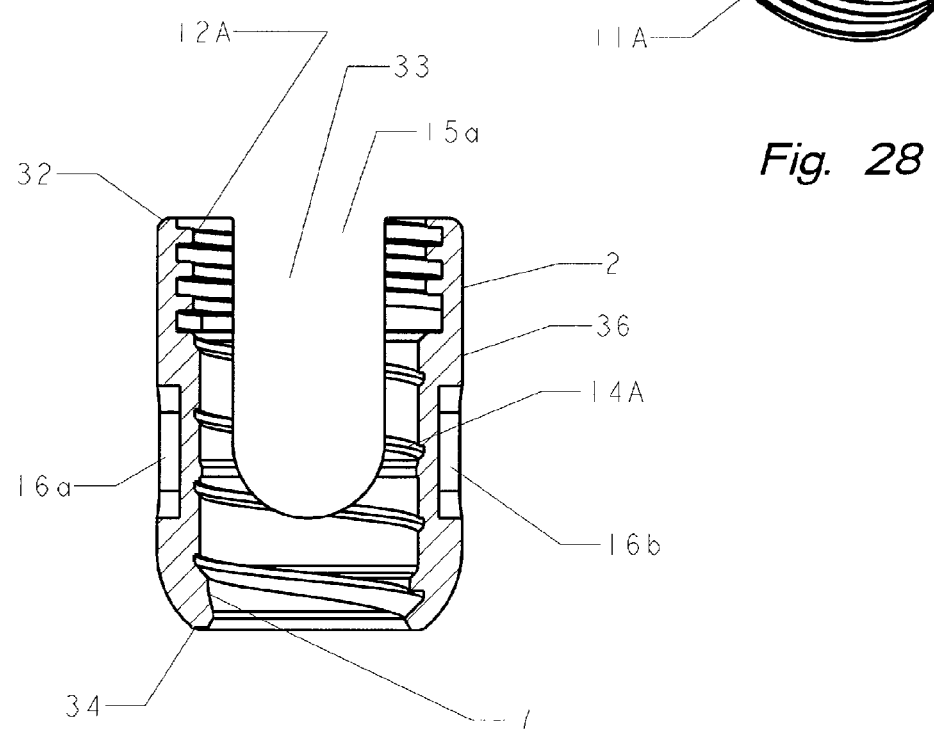
Fig. 29

POLYAXIAL BONE SCREW

CROSS REFERENCE TO RELATED APPLICATIONS

This application is a Continuation-In-Part of U.S. patent application Ser. No. 11/749,615, filed May 16, 2007, entitled, "Polyaxial Bone Screw", the entire disclosure of which is incorporated herein by reference.

FIELD OF THE INVENTION

This invention is directed to spinal implant systems and, in particular, to a multi-component adjustable implant system and polyaxial bone screw and connector kit.

BACKGROUND OF THE INVENTION

For individuals with spinal pathologies, the development of spinal fixation devices represents a major medical breakthrough. Surgically implanted fixation systems are commonly used to correct a variety of back structure problems, including those which occur as a result of trauma or improper development during growth. These fixation systems typically include one or more stabilizing rods aligned in a desired orientation with respect to a patient's spine. Additionally, anchoring screws are inserted into the patient's spinal bones, and a series of connectors are used to rigidly link the rods and anchors.

A variety of designs exist, with each design addressing various aspects of the difficulties that arise when one reshapes an individual's spine to follow a preferred curvature. Unfortunately, known spinal implant systems often correct one set of problems only to create new ones.

Common to spinal implant systems is the necessity for proper anchoring to the bone so as to provide support for the aforementioned components. While bone screws are commonly used for anchoring, they are limited in their positioning due to the design of component pieces. Numerous patents are directed to component design in order to accommodate the bone screw, yet few patents are directed to making the assembly as compact as possible to lessen the stress on the individual who must live with the object within their body.

For this and other reasons, screws located in bone structure typically use a specially designed clamp to attach to a component such as an alignment rod. A problem with specially designed clamps is that bone structure cannot be determined until the patient's bone is exposed causing the necessity of a large inventory of various sized clamps to be on hand during surgery because the screws and clamps are typically pre-assembled with respect to size, e.g. a larger screw requires a larger clamp, during assembly of the screw and the saddle. Typically a screw is passed through an aperture at the bottom portion of a saddle, therefore the aperture must be large enough for passage of the threads, the spherical portion of the screw must be larger than the threads and the aperture so that the spherical portion will contact the seat which extends around the aperture. A further limitation of the prior art relates to the requirement of a larger saddle for larger screw diameters. The larger saddle complicates the placement of the screw to prevent impingement to adjacent body structures.

In the current art, even if a clamp combination is predicted, insertion of the screw may still require angular insertion due to muscle or tender nerve locations. The result is a bone screw which exerts unpredictable forces upon attachment to component connectors. Further, any movement of muscle and other tissue increases the difficulty of the operation and can be a major trauma to a person.

A conventional bone screw consists of a single shaft with a coarse thread at one end for threading into the bone and a machine thread at the other end for coupling to components. Another type of bone screw has a U-shaped top which acts as a saddle for attachment to an alignment rod. If the screw is placed incorrectly for any reason, the rod clamp must be made to accommodate the position.

A number of patents exist which demonstrate the reliance on the saddle type screw support and various designs to accommodate the problem.

U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion design for threadingly engaging a semi-spherical cup for use with a specially designed alignment rod. The alignment rod having spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are adapted with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employ connectors that join the support rods and anchoring screws. The connectors eliminate unwanted relative motion between the rod and the screws, thereby maintaining the patient's spine in a corrected orientation.

Unfortunately, although these so-called rigid screw fixation systems can alter the curvature of a patient's spine, they can also be difficult to install. In this type of system, the anchoring screws must be secured in a region that is strong/rigid enough to support the characteristically-large loads typically transferred from the support rods. As a result, the number of suitable anchoring locations is limited. Typically, these screws are anchored into the posterior region of a patient's spinal column or into pedicle bone. With rigid screw systems, installation requires bending a support rod into a path that will not only correct the shape a patient's spine but that will also engage each of the installed anchoring screws. Achieving a proper fit between all of the components while contending with the constraints encountered during surgery is often difficult. In severe cases, a suitable fit may not be achieved and the surgery will be unsuccessful.

Additionally, the nature of the installation process required for rigid screw fixation systems often subjects the system components to pre-loading that unduly stresses the interface between the patient's bone and the employed anchoring screws. With these designs, as a patient moves about during daily life, the system components may become separated from the supporting bone. Corrective surgery to reattach anchoring screws exposes an already-weakened region to additional trauma and presents the risk of additional damage.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths. Unfortunately, some adjustable fixation systems tolerate only limited amounts of relative adjustment between components, operating best when loaded in one of several preferred arrangements. As a result, many prior art adjustable fixation systems are suitable for only a few situations.

Additionally, many adjustable fixation systems are prone to post-surgery component loosening. As a patient moves about during day-to-day living, their spine is subjected to a seemingly-endless amount of dynamic loading. Almost all activity requires some form of back motion; over time, this cyclic movement tends to work the components of many adjustable fixation systems loose.

Some adjustable spinal fixation systems include locking mechanisms designed for long-term, post-surgery securement of the system components. Although capable of being locked in place, these systems are often difficult to secure, requiring an excess of tools during the installation process. The need for extra tools, such as those required to shave, to apply anti-torque, or crimp key portions of a fixation system, increasing surgical risk by adding complexity and increasing the number of required steps. Although locking-component fixation systems exist, many of them unduly increase the dangers of back implant surgery to an unacceptable level.

Hardware-intensive fasteners are disclosed in U.S. Pat. No. 5,549,608, in which anchoring screws are fitted with wrenching flats that allow an anchoring screw to be attached to a patient's spinal bone with the flats being trimmed away once the screw is in place. Clamping nuts are then used to secure the anchoring screws to included stabilizing rods.

Additionally, many spinal fixation systems do not permit component repairs. If, for example, a threaded portion of a connecting member becomes stripped or cross-threaded, the entire connector must be slid off of the associated stabilizing rod. Often, such removal produces an undesirable domino-effect, requiring that several connectors be slid off to allow removal of the damaged connector. Such requirements add unnecessary difficulty to an already-complex procedure.

The bone screws shown and described in U.S. Pat. No. 5,628,740 and U.S. Pat. No. 6,050,997 have a bone screw with a spherical cavity in the proximal end. A toggle bolt with a spherical distal end is inserted into the cavity in the bone screw. A collet is forced into the spherical cavity superior to the spherical end of the toggle bolt. A support collar or attachment cap is placed over the toggle bolt and tightened down. This forces the retention collet to engage the spherical portion of the toggle bolt and the inside of the spherical cavity locking the toggle bolt in a selected angular disposition. This system requires extremely accurate machining of the threaded components to result in an optimum frictional fit. Further, because the collet is a ring, with a fixed inner diameter, there is only one correct size for the spherical components. Finally, any deformation of the ring will lessen the over-all frictional contact by creating wrinkles or ridges on the collet.

U.S. Pat. No. 4,419,026 to Leto discloses a split ring camming internal locking device used with telescoping tubular members for transporting liquids. The ring is split for flexing to fit around the internal tube and for resiliently sealing against the external tube.

The bone screw described in U.S. Pat. Nos. 7,128,743 and 6,537,276 and 6,261,287 and 6,090,110 includes an annular head with an opening and a slot. Each slot extends into the opening and is provided with internally threaded portions. A securing screw is screwed into the slot. A relatively stiff threaded rod is inserted into the opening the pedicle screw and is secured in place by the securing screws. In an alternate embodiment the screw includes a shaft with an upper end formed as a ball. A cage cooperates with the ball and further includes a passage to receive a threaded rod. The cage also includes a threaded portion for receiving a securing screw for securing the rod to the cage and screw.

The bone screw described in U.S. Pat. No. 6,726,689 includes a locking or securing element wherein the threads on the implant member and securing element are configured to prevent splaying of the arms of the implant member.

Thus, what is needed is a spinal fixation system that includes the advantages of known devices, while addressing the shortcomings they exhibit. The system should allow component adjustment during installation, thereby enabling satisfactory correction of a wide variety of spinal deformities. The system should also include a component locking mechanism that is simple and reliable. The system should also include mounting hardware that secures with a minimum of tools and that allows modular replacement of components damaged during installation. The system should also include tools and components for the locking mechanism developing a compression fit between components without additional torque on the bone-screw interface.

SUMMARY OF THE INVENTION

The present invention is a fastening system for bone screws used in spinal fixation systems for reshaping the spine of a patient. The bone screw has threads on one end for anchoring in the spine. The other end has a spherical head with a multi sided recess formed therein for engagement with an appropriate driving tool. The stabilizing rods are shaped and aligned to impart a preferred curvature to a patient's spine.

Attaching each anchoring assembly to a stabilizing rod forces a patient's back into a surgeon-chosen shape. Stabilizing rods may be used singly, or in pairs, depending upon the type of correction required. The rods vary in size, but typically extend between at least two vertebrae.

During the surgical procedure it is common to employ screws of varying diameter threads dependent on the shape and quality of the bone formations presented by the patient. Likewise it is important that the overall size and shape of the connecting elements be kept to an absolute minimum without jeopardizing the structural integrity of the components. In addition, it is also very desirable from a cost and safety perspective to minimize the number of component parts that are maintained in inventory and subsequently brought into the operating room to be used during the procedure.

Accordingly, it is an objective of the present invention is to provide a fastener system for polyaxial bone screws of varying size capable of cooperation with a common base member whose profile is minimized while at the same time optimizing the structural integrity of the base member.

It is another objective of the present invention to provide a polyaxial bone screw assembly for a spinal fixation system that permits component adjustment during installation, thereby enabling satisfactory correction of a wide variety of spinal deformities.

It is still another objective of the present invention to provide a simple, easy to use, reliable and cost effective implant system.

It is an additional objective of the present invention to provide a bone screw assembly that includes a fastener member that is simple and reliable.

It is yet another objective of the present invention to provide a spinal fixation system that includes mounting hardware which requires a minimum number of tools.

It is also an objective of the present invention to provide a spinal fixation system that allows modular replacement of damaged components.

Still another objective is to teach the use of a rod clamping device having a polyaxial bone screw wherein the rod claim saddle permits passage of a bone screw having a diameter larger than the cavity provided in a saddle.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 1 is a pictorial view of the spinal fixation system of the present invention;

FIG. 2 is a pictorial view of the anchoring device and associated components of the instant invention utilizing one of the larger screw elements;

FIG. 3 is a pictorial view of the anchoring device and associated components of the instant invention utilizing a screw of a smaller dimension than that shown in FIG. 2;

FIG. 10 is a perspective view of the head member of the present invention;

FIG. 11 is a cross sectional view of the head member of the present invention;

FIG. 12 is a pictorial view illustrating the set screw of the present invention;

FIG. 13 is a perspective view of the cap member of the present invention;

FIG. 14 is a side view of the cap member of the present invention;

FIG. 15 is a sectional view of the cap member seated within the head member (the screw being omitted for purposes of clarity only as will described in the detailed description to follow);

FIG. 16 is an isometric view of the head of the instant invention;

FIG. 17 is an isometric view of the cap member of the present invention;

FIG. 18 is a pictorial view of the screw assembly illustrating the sixty degrees of polyaxial motion of the screw with respect to the head member; and FIGS. 19 through 22 are perspective views of four different sized screws (by way of example only) that can be used with the polyaxial screw system.

FIG. 23 is a perspective view of an additional embodiment of the spinal fixation system.

FIG. 24 is a side elevation view of the spinal fixation system of FIG. 23.

FIG. 27 is an enlarged perspective view of an additional form of rod base member.

FIG. 28 is an enlarged perspective view of an additional form of set screw.

FIG. 29 is a cross sectional elevation view of the addition form of rod base member of FIG. 27.

Like numbers used throughout this application represent like or similar parts and/or construction.

DETAILED DESCRIPTION OF THE INVENTION

Figure 4:
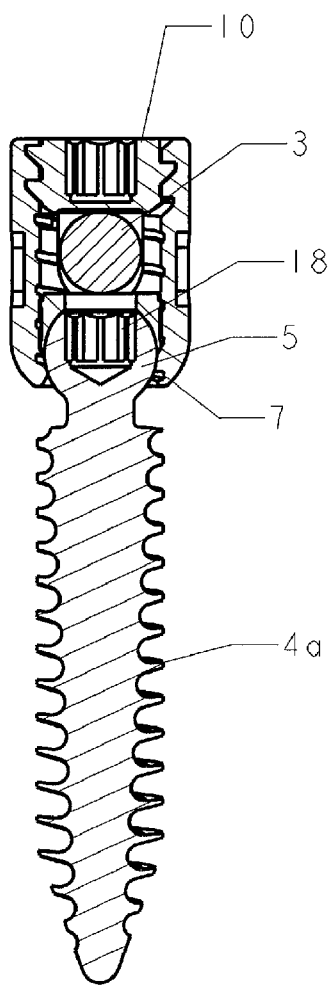
FIG. 4 is a cross sectional view of the larger polyaxial bone-engaging screw and associated components in an assembled condition.
Figure 6:
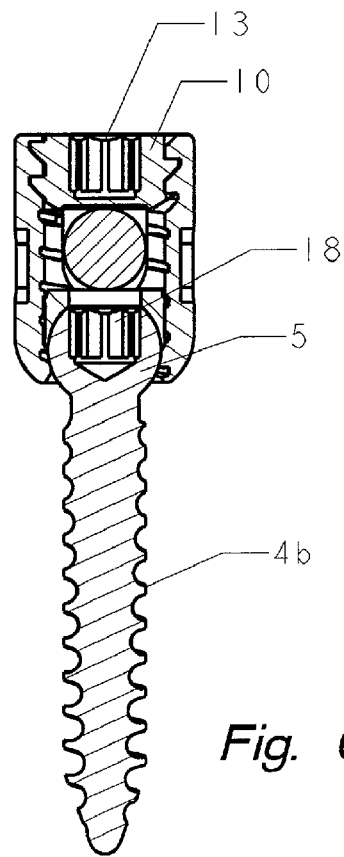
FIG. 6 is a cross sectional view of a smaller polyaxial bone-engaging screw and associated components in an assembled condition.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Now with reference to FIG. 1, the spinal fixation system 1 includes a plurality of polyaxial screws 4 each in cooperative relationship to a rod base member 2 for fixedly securing a stabilizing rod 3.

FIGS. 2 and 3, illustrate two anchoring devices wherein the diameter of the threaded shank portion 6a of the polyaxial screw 4(a) in FIG. 2 (D1) is larger than the threaded shank portion 6(b) the polyaxial screw 4(b) illustrated in FIG. 3 (D2).

FIGS. 4, 5, 6 and 7 illustrate polyaxial screws 4(a) and 4(b) each having a spherical head 5. The spherical head 5 includes a tool socket 18 at the top portion thereof to receive a tool (not shown) constructed and arranged to transfer rotary and/or linear force to thread the screw into the patient's bones. Rod base member 2, which is also shown in more detail in FIGS. 10, 11, 15, and 16, is generally cylindrical in shape and includes a pass-through aperture that extends between the upper portion 32 and an aperture in the lower portion 34. The rod base member 2 also includes two diametrically opposed U-shaped slots 15(a) and 15(b), as shown in detail in FIG. 10, in the side wall 19 which are open at the upper end 32 of the rod base member 2 and extend downwards towards the lower portion 34 of the rod base member. The side wall 19 includes a pair of arms 24A, B that have edges defining portions of the slots 15(a), (b) and the slots forming a rod receiving channel. The rod base member 2 also includes a helical seating surface 7 at the lower portion 34 of the rod base member. The spherical head 5 of the polyaxial screw, 4a or 4b, is designed to operatively cooperate with the helical seating surface 7 on the rod base member 2 for polyaxial movement of the screw with respect to the rod base member 2. The helical seating surface 7 provides multiple points of contact not necessarily in the same plane thereby reducing the chances of slippage between the spherical head 5 and helical bearing surface 7 after the parts are securely assembled and the set screw is tightened. It should also be noted that seats having a shape other than helical could be used without departing from the scope of the invention which may include, but should not be limited to, frusto conical, spherical, sharp edges, radiused edges, segmented and suitable combinations thereof. The polyaxial screw 4 is properly positioned within rod base member 2 against the seat 7. A cap member 8, which is also shown in more detail in FIGS. 13, 14 and 17, can then fit into the lower portion of the pass-through aperture 33. The cap member 8 is generally cylindrical in shape and is provided with a generally flat 30, cylindrical (not shown) or other suitable surface on one end and generally hollow semi spherical surface 17 on the opposite end sized for cooperation with the head 5 of the screw 4. The cap member 8 further includes an aperture 9 which extends between the end surface 30 of the cap member and the semi spherical surface 17 on the opposite end of the cap member. Aperture 9 permits insertion of a driving tool (not shown) into socket 18 on the head 5 of the polyaxial screw for threading the screw 4 into the patient's bone.

Referring to FIGS. 13, 14 and 17, the cap member 8 further includes resilient friction fingers 20 on opposite sides of the cylindrical walls as well as annular ridges 21 and 22 around the circumference of the cylindrical cap member located near the top and bottom thereof. The rod base member 2 includes an annular interference diameter 23 that cooperates with annular ridge 21 of the cap member 8 once the cap member is pressed past the interference diameter 23 to prevent the cap from falling out of position once installed. In addition, friction fingers 20 serve to maintain the semi spherical seat 17 and the spherical head 5 in operative engagement wherein the screw has polyaxial freedom of motion and yet will hold a particular set orientation between the screw and the head until a sufficient amount of force is applied thereto. This particular feature assists the surgeon in positioning the rod base member relative to an inserted bone screw prior to final securement of the rod member 3.

A set screw 10, shown in more detail in FIG. 12, is generally cylindrical in shape with external threads 11 on the cylindrical surface and opposed generally flat ends. One of the flat ends of the set screw 10 includes a tool socket 13 to provide operative engagement with an appropriate driving tool. The internal cavity of the rod base member 2 is provided with threads 12 having a form, pitch and size to conform to the threads 11 of the set screw. In a most preferred embodiment the threads are buttress style threads that may include a back tapered upper surface to provide anti-splaying characteristics to the rod base member 2. However, it should be noted that other thread types suitable for securing the instant assembly together may be utilized without departing from the scope of the invention. The set screw 10 will be torqued into the rod base member 2 with a force of approximately 100 inch pounds to ensure that the connector and rod member are firmly locked in place. The internal cavity of the rod base member 2 also includes threads 14 which extend from the lower end of threads 12 through to the lower end of the rod base member 2. The purpose of these threads will be discussed in more detail with respect to FIGS. 5, 7 and 9.

Referring to FIGS. 2 and 3, polyaxial screws 4a and 4b are illustrated each having threads of varying diameter in an assembled condition with a stabilizer rod 3, a rod base member 2, a cap member 8 and a set screw 10.

Figure 5:
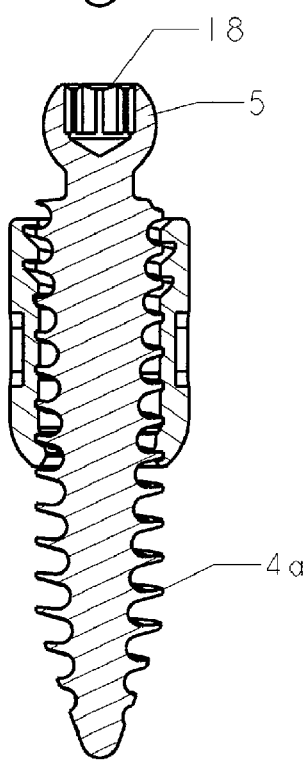
FIG. 5 is a section view of a polyaxial bone-engaging screw with the head member as shown in FIG. 4 during an intermediary stage of assembly.
Figure 7:
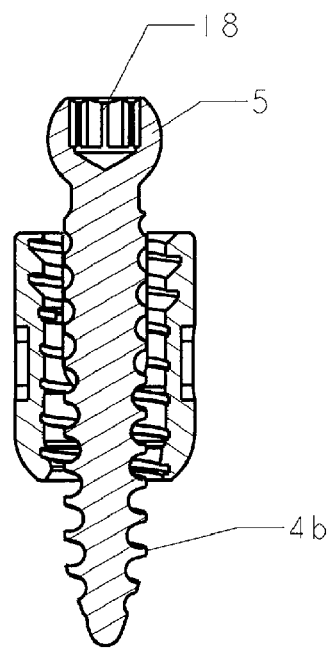
FIG. 7 is a section view of a polyaxial bone-engaging screw as with the head member as shown in FIG. 6 during an intermediary stage of assembly.
Figures 8, 9:
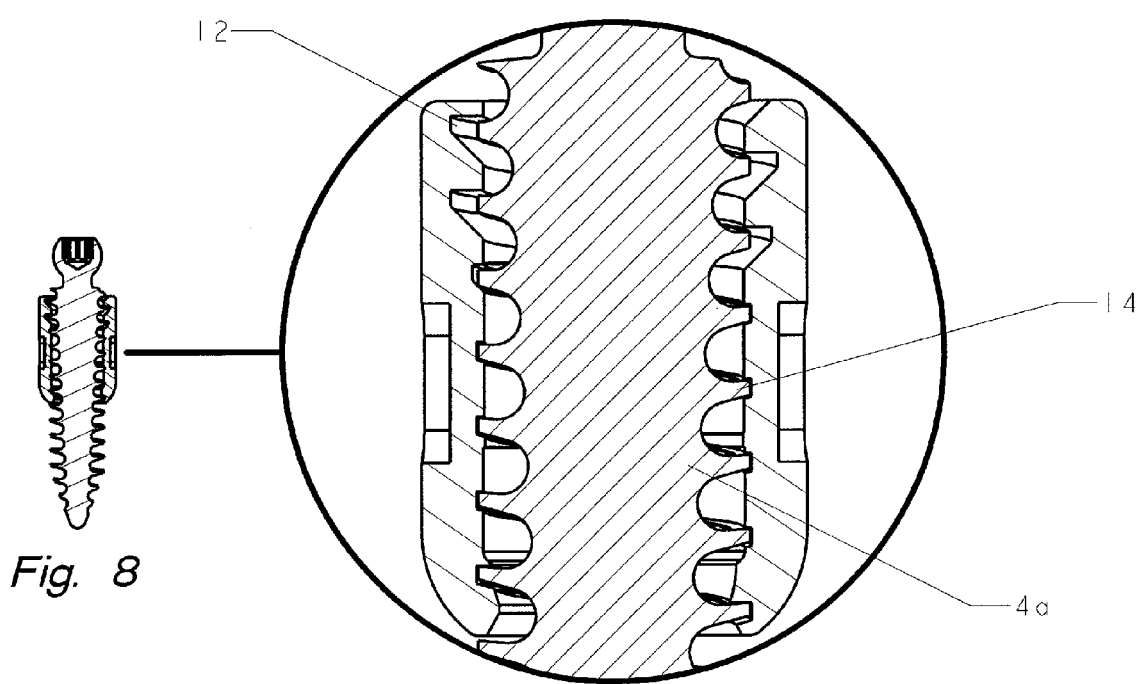
FIG. 8 is a cross sectional view of the polyaxial screw and head member during an intermediary stage of assembly.
FIG. 9 is an enlarged sectional view of the head member and the polyaxial screw and the relationship between the threads of the polyaxial screw and the threads on the interior wall of the head member, as shown in FIG. 8.
Figure 25:
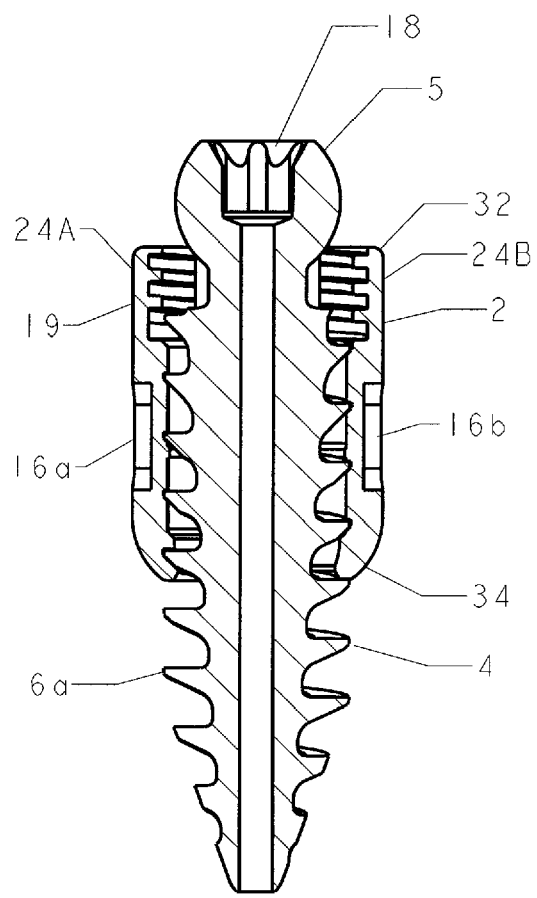
FIG. 25 is a cross sectional elevation view of the spinal fixation system of FIG. 24.

Referring to FIGS. 5 and 7, the unique relationship between the rod base member 2 and the polyaxial screws 4(a) and 4(b) and their respective threads 6(a) and 6(b) is illustrated. Turning to FIG. 5, it can be seen that as the larger diameter screw thread is inserted into the interior cavity of rod base member 2, the threads 6(a) on screw 4(a) include substantially the pitch to engage the screw threads 12 on the upper portion of the interior cavity and subsequently engage threads 14 which extend from the lower end of threads 12 through to the lower end of rod base member 2. In this manner, the polyaxial screw can be screwed into position wherein the spherical head 5 rests on the helical seating surface 7. It should be noted that this construction permits a bone screw having a larger diameter than the pass through aperture 33 of the rod base member 2 to be inserted therethrough, whereby the spherical head portion of the bone screw will still engage the seat portion 7 of the rod base member 2. It should also be noted that the thread form and pitch of the bone screw do not have to match the exact thread form and pitch of the rod base member for operation, the pitch and form of the thread on the bone screw need only be constructed and arranged to threadably pass through the pass through aperture 33 without significant interference between the two components. FIG. 7 illustrates the relationship between the rod base member 2 and a polyaxial screw 4(b) with a smaller diameter screw thread 6(b). As can be seen in FIG. 7, there is sufficient clearance between the outer diameter of the threads 6(b) and walls of the pass-through aperture to easily allow the screw to be inserted through the pass-through aperture 33 until the head 5 rests on the helical seat 7 of the rod base member 2. It should be noted that this feature also permits the interchangeability of screws of varying diameter while utilizing the same rod base member (s), cap member (s), and set screw (s). This construction also permits the instant invention to be provided in a kit form wherein a rod base member, cap member and set screw may be provided with a plurality of bone screws having different outer diameters allowing a surgeon to choose a bone screw for the specific patient condition. This feature also allows a surgeon to increase the diameter of screw in cases where the smaller diameter screw fails to achieve the proper purchase to the bone during tightening of the bone screw or where the patient's bones are more fragile or deteriorated than expected.

FIGS. 10, 11, 15 and 16 illustrate the rod base member 2 and the U-shaped slots 15(a) and 15(b) as well as threads 12 and 14 within the internal cavity. Recesses 16(a) and 16(b) on the external walls of the head 2 are designed to cooperate with assembly tools to provide forces to counteract the tightening of the set screw. In this manner, loads exerted on the set screw are substantially prevented from being transferred to the bone screw bone interface.

FIG. 18 illustrates the range of infinite angular adjustment between the rod base member 2 and the polyaxial screw 4 prior to tightening of set screw 10. It is contemplated, in a non-limiting embodiment, that the screw be capable of about 60 degrees of polyaxial motion within a 360 degree range of movement.

FIGS. 19 through 22 illustrate polyaxial screws 4 each having threaded sections of different external diameter showing, by way of example only, four separate screws; 8.5 mm (FIG. 19), 7.5 mm (FIG. 20), 6.5 mm (FIG. 21) and 5.5 mm (FIG. 22). It should be noted, that the spherical head portion 5 of the bone screw(s) 4 is substantially the same size across the full range of bone screw diameters.

The spinal fixation system 1 (FIG. 1) is assembled in the following manner. A polyaxial screw 4 is either slid through or threaded through the pass-through aperture of a rod base member 2 until the spherical head 5 of the polyaxial screw 4 rests on the helical seating surface 7 at the lower end portion of the rod base member. Thereafter the cap member 8 is positioned in the pass-through aperture 33 of the rod base member in such a manner so that the generally hemispherical surface 17 of the cap member mates with the upper portion of the spherical head 5 of the bone screw. This step also engages the annular ridges 21, 22 with the interference diameter 23 in the pass-through aperture. A tool is then inserted through aperture 9 and into tool socket 18 on the top of spherical head 5 for threading the screw into the patient's bone. One or more additional screw(s) are inserted into the patient's bones in a similar fashion. A stabilizing rod 3 is positioned within the U-shaped slots 15(a) and 15(b) of each rod base member 2. The rod 3 bears against the flat surface of the cap member 8. A set screw 10 is threaded into the upper end of each rod base member 2. Once the angular orientation of the stabilizing rod with respect to the polyaxial screws is properly established the set screws are securely tightened so as to fix the stabilization rod in a proper position.

Referring to FIGS. 1 through 22, the spinal fixation system 1 is preferably formed from rigid, biocompatible materials. One such preferred material is titanium; however, other materials well known in the art may also be used. It should also be noted that any or all of the components could be made from bio-resorbable materials or could be coated with bone growth materials that are well known in the art without departing from the scope of the invention.

FIGS. 23-29 illustrate additional embodiments of the invention similar to those shown in FIGS. 1-22 and are similar in construction and use. The illustrated set screw 10 and rod base member 2 are similar but have differences as described below, particularly with reference to the upper end of the rod base members 2 and the set screws 10. Now with reference to FIG. 23, the spinal fixation system 1 includes a polyaxial screw 4 in cooperative relationship to a rod base member 2 for fixedly securing a stabilizing rod 3.

Figure 26:
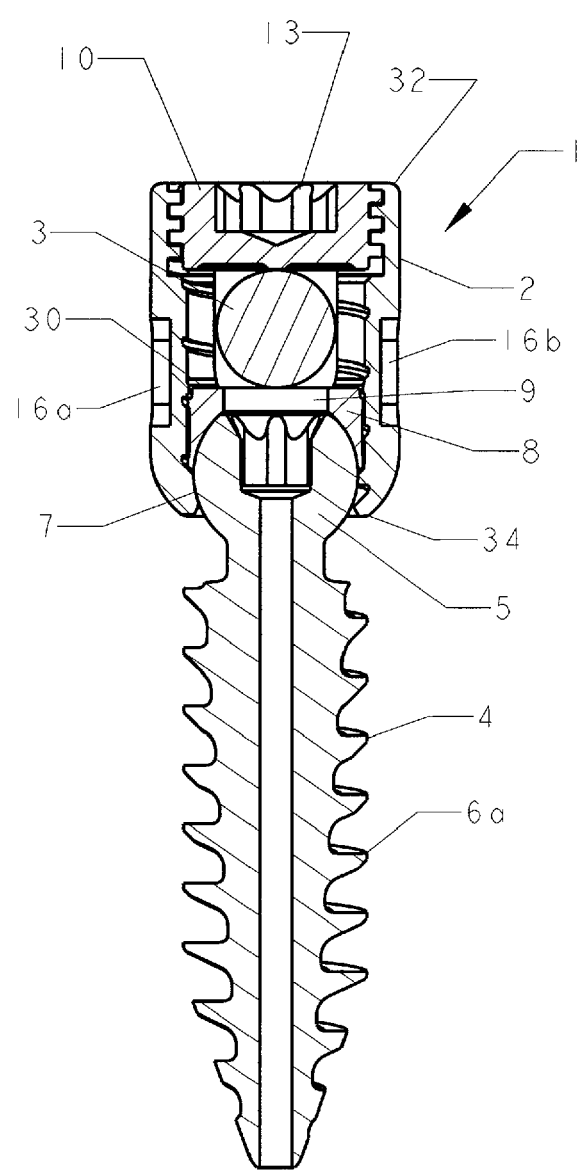
FIG. 26 is a cross sectional elevation view of the spinal fixation system of FIG. 23.

FIGS. 23 and 26, illustrate a fixation system 1 wherein the screw 4 has a diameter of the threaded shank portion 6a as described above but could also have a threaded shank portion 6(b) also as described above cooperating with the base member 2.

The illustrated polyaxial screw 4 has a spherical head 5. The spherical head 5 includes a tool socket 18 at the top portion thereof to receive a tool (not shown) constructed and arranged to transfer rotary and/or linear force to thread the screw 4 into a patient's bone. Rod base member 2, FIGS. 27, 29, is generally cylindrical in shape and includes a pass-through aperture 33 that extends between the upper portion 32 and an opening in the lower portion 34. The rod base member 2 also includes two diametrically opposed U-shaped slots 15(a) and 15(b) in the side wall 19 which are open at the upper end of the rod base member 2 and extend downwards towards the lower portion 34 of the rod base member. The side wall 19 includes a pair of arms 24A, B that have edges defining portions of the slots 15(a), (b) and the slots forming a rod receiving channel. The rod base member 2 also includes a seating surface 7 at the lower portion 34 of the rod base member as described above. The spherical head 5 of the screw 4, is designed to operatively cooperate with the seating surface 7 on the rod base member 2 for polyaxial movement of the screw 4 with respect to the rod base member 2. It should also be noted that seat 7 can have any suitable shape such as helical, frusto conical, spherical, sharp edges, radiused edges, segmented and suitable combinations thereof. The screw head 5 is properly positioned within rod base member 2 against the seat 7. A cap member 8, FIG. 26, can then fit into the lower portion of the pass-through aperture 33. The cap member 8 is generally cylindrical in shape and is provided with a generally flat, circular surface 30, or other suitable surface on one end and generally hollow seating surface 17 on the opposite end sized and shaped for cooperation with the head 5 of the screw 4. The cap member 8 further includes an aperture 9 which extends between the end surface 30 and the semi spherical surface 17 on the opposite end of the cap member. Aperture 9 permits insertion of a driving tool (not shown) into socket 18 on the head 5 for threading the screw 4 into the patient's bone.

The cap member 8 is as described above and can include resilient friction fingers 20 on opposite sides of the cylindrical walls as well as annular ridges 21 and 22 around the circumference of the cylindrical cap member located near the top and bottom thereof. The rod base member 2 includes an annular interference diameter 23 that cooperates with annular ridge 21 of the cap member 8 once the cap member is pressed past the interference diameter 23 to prevent the cap from falling out of position once installed. In addition, friction fingers 20 serve to maintain the seat 17 and the head 5 in operative engagement wherein the screw 4 has polyaxial freedom of motion and yet will hold a particular set orientation between the screw and the head until a sufficient amount of force is applied thereto.

A set screw 10, shown in FIGS. 23, 26, 28, is generally cylindrical in shape with external threads 11A on the cylindrical surface and opposed ends that are shown as generally flat. One of the flat ends of the set screw 10 includes a tool socket 13 to provide operative engagement with an appropriate driving tool. The internal cavity of the rod base member 2 is provided with threads 12A adjacent to and extending into the cavity from the end 32. The threads 12A have a form, pitch and size to conform to the threads 11A of the set screw 10. In a preferred embodiment the threads 11A, 12A are different from the threads 6a and can be any suitable machine thread having a pitch less than the pitch of the threads 6a. The threads 11A, 12A have a pitch preferably finer than about 13 thread per inch and preferably finer than about 16 threads per inch. Any suitable thread shape may be provided such as Acme, square or any other suitable machine thread shape. A thread shape to provide anti-splaying characteristics as described above to the rod base member 2 may also be used. The threads 12A in the rod base member 2 extend inwardly from the end 32 about ⅓ the length of the aperture 33. The internal cavity of the rod base member 2 also includes the threads 14A which extend from the lower end of threads 12A toward the lower end 34 of the rod base member 2. In a preferred embodiment, the remainder of the length or a substantial portion of the remainder of the aperture 33 may have threads 14A compatible with the threads 6A and are different from the threads 11A, 12A. The threads 14A have a pitch preferably coarser than about 10 threads per inch and more preferably coarser than about 8 threads per inch. The threads 6A may interfere with the threads 14A, 12A when the screw 4 is installed in the rod base member 2 as described above. As shown, the threaded shank with the threads 6A has a decreasing thread diameter toward the distal end 40 of the shank. The threads 11A, 12A have a substantially uniform thread diameter along the length of the respective threaded sections. The set screw 10 will be torqued into the rod base member 2 with a force of approximately 100 inch pounds to ensure that the connector and rod member are firmly locked in place.

The screw 4 has threads 6 of varying diameter in an assembled condition with a stabilizer rod 3, a rod base member 2, a cap member 8 and a set screw 10.

Referring to FIGS. 5 and 7, the unique relationship between the rod base member 2 and the polyaxial screws 4(a) and 4(b) and their respective threads 6(a) and 6 (b) is illustrated. That description is applicable to the screw 4 and threads 6A and 6B and their variants as described above.

FIGS. 27, 29 illustrate the rod base member 2, the U-shaped slots 15(a) and 15(b) as well as threads 12A and 14A within the internal cavity. Recesses 16(a) and 16(b) on the external walls of the base member 2 are designed to cooperate with assembly tools to provide forces to counteract the tightening of the set screw. In this manner, loads exerted on the set screw are substantially prevented from being transferred to the bone screw bone interface.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal fixation system for orthopedic rod implantation, comprising:
   a bone screw having a threaded shank portion and a substantially spherical head portion;
   a rod base member having a pair of upright spaced apart arms defining a U-shaped channel, said rod base member having an upper pass through aperture and a lower pass through aperture and an internal cavity extending between said upper pass through aperture and said lower pass through aperture, said internal cavity including a threaded surface that extends the length of said internal cavity from said upper pass through aperture to said lower pass through aperture to allow said threaded shank portion to pass through said internal cavity while retaining said spherical head portion, said threaded surface including a first thread portion having a first thread configuration and a second thread portion having a second thread configuration, said first thread configuration being different than the second thread configuration;
   a monolithic cap member positioned along an end of said spherical head portion, said cap member providing a spherical seating surface for an upper surface of said spherical head and a support base for a stabilizing rod placed within said U-shaped channel, wherein the cap member includes annular ridges on the cylindrical wall of the cap member at the top and bottom thereof; and
   a set screw threadably engageable along said threaded surface of said internal cavity for engaging said stabilizing rod against said cap member wherein said cap member secures said rod base member in a fixed position by frictional engagement with said spherical head portion of said bone screw.

2. The spinal fixation system of claim 1 wherein said threaded surface is adapted to engage said set screw and sized to allow unobstructed insertion of said bone screw threaded shank.

3. The spinal fixation system of claim 1 wherein said lower pass-thru aperture includes a seat member receptive to a lower surface of said spherical head.

4. The spinal fixation system of claim 1 wherein said U-shaped channel is further defined as two diametrically opposed openings on the walls thereof wherein the stabilizing rod is positioned within the two shaped openings.

5. The spinal fixation system of claim 1 wherein the threads on said set screw are configured to prevent splaying of said rod base member.

6. The spinal fixation system of claim 1 wherein said monolithic cap member is generally cylindrical in shape and is provided with a flat surface on one end and generally semi spherical surface on an opposite end.

7. The spinal fixation system of claim 6 wherein the cap member further includes an aperture which extends between the flat surface on one end of the monolithic cap member and the semi spherical surface on the opposite end of the cap member.

8. The spinal fixation system of claim 1 wherein the monolithic cap member further includes resilient friction fingers on the cylindrical wall thereof which are in opposed relationship to one another.

9. The spinal fixation system of claim 1 wherein the threads of the first threaded portion are finer than the threads on the second threaded portion.

10. The spinal fixation system of claim 1 wherein the rod base member includes an interference diameter within the interior cavity that cooperates with the top annular ridge to prevent the monolithic cap member from backing up.

11. The spinal fixation system of claim 1 wherein the monolithic cap member includes an aperture within the spherical seat.

12. The spinal fixation system of claim 1 wherein the spherical head of the polyaxial screw includes a multi sided tool socket.

13. The spinal fixation system of claim 1 wherein the set screw includes a top and a bottom wall, said bottom wall being generally flat and in abutting relationship to said stabilizing rod, said top surface being generally flat and including a multi sided tool socket in said top surface for driving said set screw.

14. A spinal fixation kit for orthopedic rod implantation, comprising:
  at least two bone screws, each said bone screw having a threaded shank portion and a substantially spherical head portion;
  a rod base member having a pair of upright spaced apart arms defining a U-shaped channel, said rod base member having an upper pass through aperture and a lower pass through aperture and an internal cavity extending between said upper pass through aperture and said lower pass through aperture, said internal cavity including a threaded surface that extends the length of said internal cavity from said upper pass through aperture to said lower pass through aperture to allow said threaded shank portion of at least one said bone screw to pass through said internal cavity while retaining said spherical head portion;
  a monolithic cap member positioned along an end of said spherical head portion, said cap member providing a spherical seating surface for an upper surface of said spherical head and a support base for a stabilizing rod placed within said U-shaped channel, wherein the cap member includes annular ridges on the cylindrical wall of the cap member at the top and bottom thereof; and
  a set screw threadably engageable along said interior threaded surface of said internal cavity for engaging said stabilizing rod against said cap member wherein said cap member secures said rod base member in a fixed position by frictional engagement with said spherical head portion of said bone screw.

15. The spinal fixation system of claim 14 wherein said threaded surface is adapted to engage said set screw and sized to allow unobstructed insertion of at least one said bone screw having a threaded shank.

16. The spinal fixation system of claim 14 wherein the threads on said set screw are configured to prevent splaying of said rod base member.

17. The spinal fixation system of claim 14 wherein said monolithic cap member is generally cylindrical in shape and is provided with a flat surface on one end and generally semi spherical surface on an opposite end.

18. The spinal fixation system of claim 17 wherein the monolithic cap member further includes an aperture which extends between the flat surface on one end of the cap member and the semi spherical surface on the opposite end of the cap member.

19. The spinal fixation system of claim 14 wherein the monolithic cap member further includes resilient friction fingers on the cylindrical wall thereof which are in opposed relationship to one another.

20. The spinal fixation system of claim 14 wherein the threads of the first threaded portion are finer than the threads on the second threaded portion.

21. The spinal fixation system of claim 14 wherein the rod base member includes an interference diameter within the interior cavity that cooperates with the top annular ridge to prevent the monolithic cap member from backing up.

22. The spinal fixation system of claim 14 wherein the monolithic cap member includes an aperture within the spherical seat.

23. The spinal fixation system of claim 14 wherein the spherical head of the polyaxial screw includes a multi sided tool socket.

24. The spinal fixation system of claim 14 wherein the set screw includes a top and a bottom wall, said bottom wall being generally flat and in abutting relationship to said stabilizing rod, said top surface being generally flat and including a multi sided tool socket in said top surface for driving said set screw.

* * * * *